Oct. 19, 1965 C. FISCHER Plant Pat. 2,562
GLADIOLUS PLANT
Filed April 15, 1964
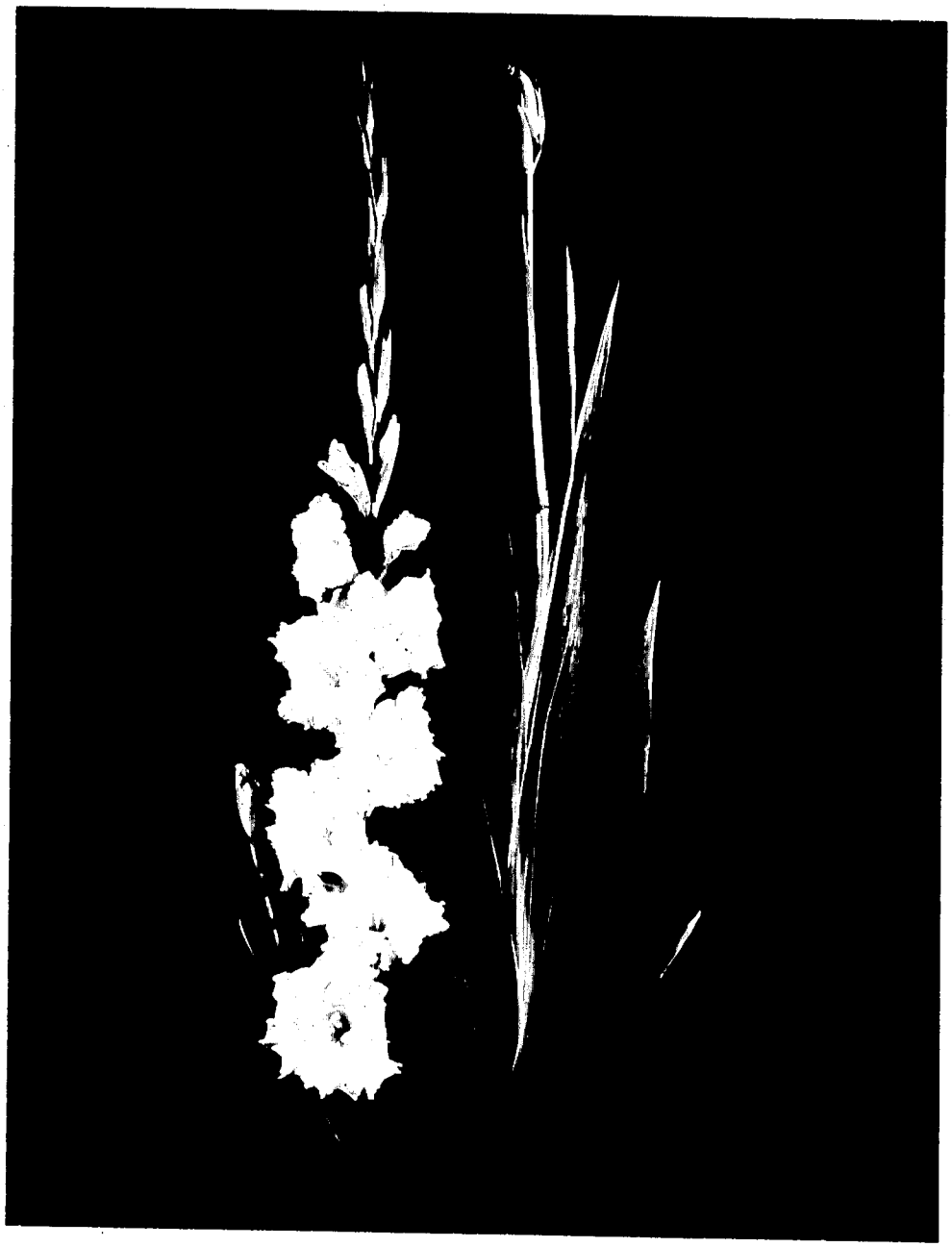
Inventor.
Carl Fischer
By: Robbs & Robb
Attorneys.

United States Patent Office

Plant Pat. 2,562
Patented Oct. 19, 1965

2,562
GLADIOLUS PLANT

Carl Fischer, St. Charles, Minn., assignor to Imperial Flowers Limited, Leamington, Ontario, Canada, a corporation of Canada Filed Apr. 15, 1964, Ser. No. 360,155
1 Claim. (Pit.—85)

The present invention relates to a new and distinct variety of gladiolus plant which was originated by me by crossing an unnamed and unpatented seedling derived from crosses of the varieties "Elizabeth the Queen," "Rose O'Day" and "Gloaming" (all unpatented) with the variety "Innocence" (unpatented).

As the result of this breeding, I have produced a new and improved gladiolus variety, as evidenced by the following unique combination of characteristics which are outstanding therein and which distinguish it from its parents, as well as from all other varieties of which I am aware:

(1) A robust habit of growth;

(2) An extremely early blooming habit;

(3) Extremely ruffled flowers which are borne on straight stems;

(4) A distinctive and attractive white flower color, said white color showing a flush of lavender or Rose Madder as the florets age; and (5) Ease of propagation.

My new variety resembles the variety known as "White Friendship" (unpatented) more than any other variety, but differs principally therefrom by a habit of blooming a few days earlier; being endowed with a much more prolific blooming habit; the flowers have a heavier substance and more heavily ruffled; and the corms are rougher but not as long-lived.

Asexual reproduction of my new variety by cormels through several generations, as performed by me at St. Charles, Minnesota, shows that the foregoing characteristics and distinctions come true to form and are established and transmitted through succeeding propagations.

The accompanying drawing shows a typical specimen flower spike and typical foliage of my new variety, with the flowers in different stages of development ranging from closed buds through partially open buds to fully open flowers, as depicted in color as nearly true as it is reasonably possible to make the same in a color illustration of this character.

The following is a detailed description of my new variety, with color terminology in accordance with the Horticultural Colour Charts issued by the British Colour Council and the Royal Horticultural Society, except where general color terms of ordinary dictionary significance are obvious:

Locality where grown and observed: St. Charles, Minnesota and Oceanside, California.

Propagation: Holds its distinguishing characteristics through succeeding propagations from cormels.

*Plant*

Growth: Extremely vigorous; run-away propagator; robust grower outdoors.

Blooming habit: Comes into bloom in about 65 days from large bulbs when grown in the northern latitudes of the United States.

Stems: Straight; slender.

*Diameter at base.*—About ⅜ inch.

*Color (at base).*—White.

Foliage: Upright; attains height of from 30 to 36 inches; individual leaves average about 1½ inches wide; prone to make numerous side spikes, and bud sheaths on side spikes tend to become petals and show white color before opening; leaves are fairly well separated from stem, making it easy to cut the flowers. Color—Medium green.

Disease resistance: Better than average resistance to the usual diseases to which gladiolus varieties are normally subject, as determined by comparison with other varities grown in Minnesota and in California.

Corms (bulbs): Rather rough; with coarse husks; old bulbs tend to have hollow centers like dougnuts and old bulbs are not as long-lived as some. Color of flesh —from Orange Buff, Plate 507/2 to Orange Buff, Plate 507/3.

*Flower*

Spike: Blossom spike averages 60 inches tall, with flowerhead averaging about 27 inches long; bears 17 or 18 buds, with about 8 buds open at one time.

Bud:

*Size.*—About 2½ inches long when opening.

*Opening.*—Usually 5 buds show color at one time; very good opener from tight bud.

Flower:

*Arrangement.*—Florets are informally arranged on the stem.

*Size.*—Individual florets average about 4½ inches in diameter.

*Form.*—Florets are round, recurved and ruffled.

*Keeping qualities.*—Good.

Petals:

*Shape.*—Round; ruffled; recurved.

*Size.*—Upper petals—about 2¼ inches wide. Lip petal—about 1½ inches wide.

*Aspect.*—Heavy substance; surface is suede-like, with creasing at edges.

*Fragrance.*—None.

*Color.*—Florets are white, with a touch of Rose Madder, Plate 23/3 dusted on the reverse of the petals; florets show a flush of lavender or Rose Madder as they age.

*Reproductive organs*

Stamens: Color—white, with creamy white pollen.

Pistil: Color—white.

I claim:

A new and distinct variety of gladiolus plant, substantially as herein shown and described, characterized particularly as to novelty by the unique combination of a robust habit of growth, an extremely early blooming habit, extremely ruffled flowers which are borne on straight stems, a distinctive and attractive white flower color, said color showing a flush of lavender or Rose Madder as the flowers age, and the ability of propagate easily.

No references cited.

ABRAHAM G. STONE, *Primary Examiner.*